United States Patent
Ren et al.

(10) Patent No.: US 10,502,714 B2
(45) Date of Patent: Dec. 10, 2019

(54) ELECTRO-MAGNETIC ACOUSTIC TRANSDUCER (EMAT) FOR BOTH LAMB AND SHEAR HORIZONTAL WAVE TRANSDUCTION

(71) Applicant: ULC Robotics, Inc., Hauppauge, NY (US)

(72) Inventors: Baiyang Ren, Hauppauge, NY (US); Junjun Xin, Ronkonkoma, NY (US)

(73) Assignee: ULC Robotics, Inc., Hauppauge, NY (US)

( * ) Notice: Subject to any disclaimer, the term of this patent is extended or adjusted under 35 U.S.C. 154(b) by 182 days.

(21) Appl. No.: 15/719,022

(22) Filed: Sep. 28, 2017

(65) Prior Publication Data
US 2019/0094184 A1    Mar. 28, 2019

(51) Int. Cl.
*G01N 29/24*    (2006.01)

(52) U.S. Cl.
CPC . *G01N 29/2412* (2013.01); *G01N 2291/0422* (2013.01); *G01N 2291/0427* (2013.01)

(58) Field of Classification Search
CPC ....... G01N 29/2412; G01N 2291/0422; G01N 2291/0427
USPC ........................................................ 73/643
See application file for complete search history.

(56) References Cited

U.S. PATENT DOCUMENTS

| | | | |
|---|---|---|---|
| 4,127,035 A * | 11/1978 | Vasile | B06B 1/04 73/629 |
| 4,248,092 A | 2/1981 | Vasile et al. | |
| 4,295,214 A | 10/1981 | Thompson | |
| 4,471,658 A | 9/1984 | Morimoto | |
| 5,747,986 A * | 5/1998 | Hristoforou | G01D 5/485 178/18.07 |
| 7,697,375 B2 | 4/2010 | Reiderman et al. | |
| 2007/0211572 A1* | 9/2007 | Reiderman | B06B 1/04 367/35 |

* cited by examiner

*Primary Examiner* — Tarun Sinha
(74) *Attorney, Agent, or Firm* — Brooks Kushman P.C.

(57) ABSTRACT

An electro-magnetic acoustic transducer (EMAT) generates both Lamb waves and shear horizontal (SH) waves or Lamb waves only. In configurations, the EMAT includes first and second coils shifted in alignment relative to one another and a magnet array overlaid over the coils. The EMAT generates a Lamb wave when the first coil is excited with an electrical current and generates a SH wave when the second coil is excited with an electrical current. In other configurations, the EMAT includes a coil and a magnet array which are movable relative to one another between a first position and a second position shifted in alignment relative to one another. The EMAT generates a Lamb wave when the coil is excited with an electrical current while in the first position and generates a SH wave when the coil is excited with an electrical current while in the second position.

20 Claims, 6 Drawing Sheets

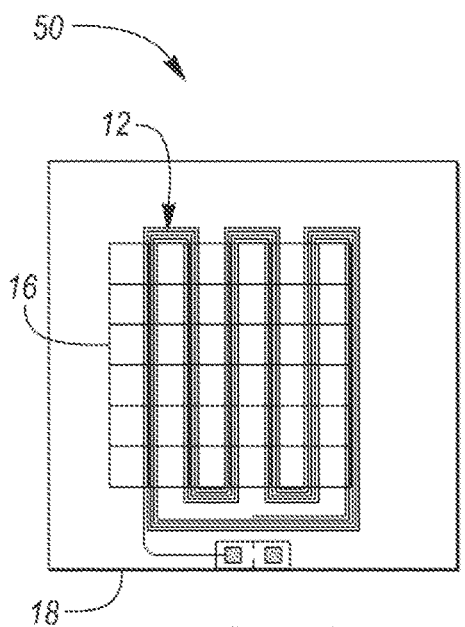
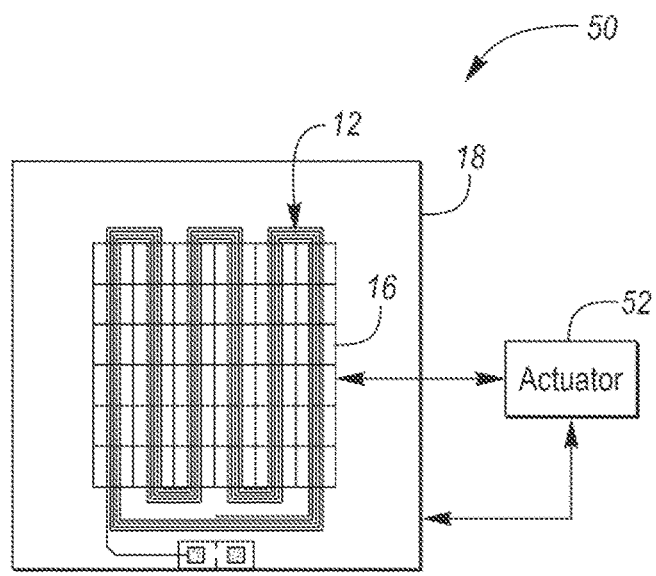
FIG. 7A  FIG. 7B
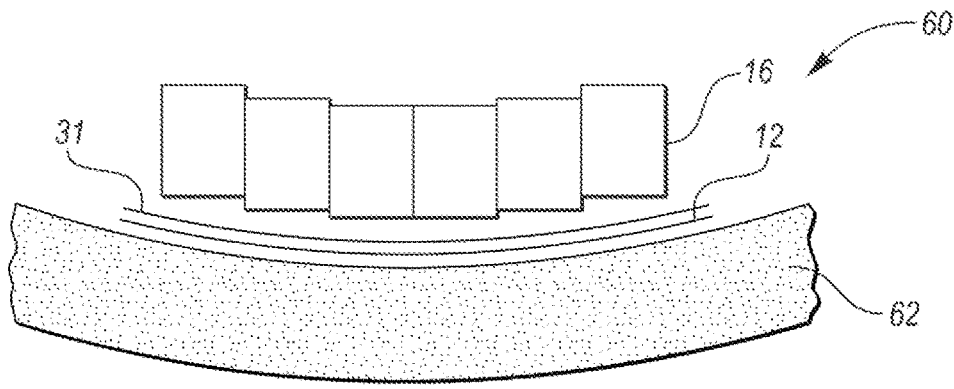
FIG. 8A
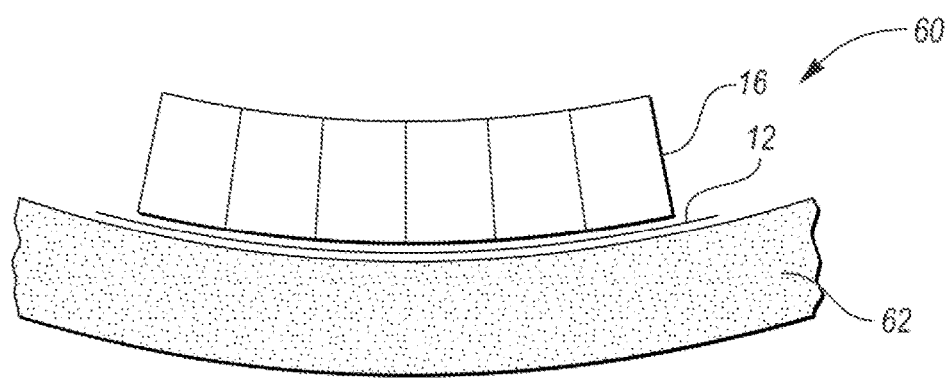
FIG. 8B

ELECTRO-MAGNETIC ACOUSTIC TRANSDUCER (EMAT) FOR BOTH LAMB AND SHEAR HORIZONTAL WAVE TRANSDUCTION

STATEMENT REGARDING FEDERALLY SPONSORED RESEARCH OR DEVELOPMENT

The present invention was made with Government support under Agreement No. DTPH5616T00004 awarded by the U.S. Department of Transportation, PHMSA. The Government may have certain rights to the present invention.

TECHNICAL FIELD

The present invention relates to an electro-magnetic acoustic transducer (EMAT) configured to generate Lamb waves and/or shear horizontal waves.

BACKGROUND

Lamb waves and shear horizontal (SH) waves are used in guided wave non-destructive evaluation (NDE). Lamb waves and SH waves have different propagation characteristics and sensitivities to different defects. It is beneficial to employ both wave types to accommodate to different working conditions and improve sensitivities to various defects.

Electro-magnetic acoustic transducers (EMATs) are used in industrial NDE because of their non-contact feature. EMATs for Lamb and SH wave excitation typically have distinctive designs such that one EMAT can only excite one type of wave. This restriction imposes limitations on the overall performance and applicability of such EMATs.

SUMMARY

An electro-magnetic acoustic transducer (EMAT) includes a magnet array, a first electrical conductor coil, and a second electrical conductor coil. The magnet array has magnets with alternating polarizations. The magnets are arranged in columns and rows so that the alternating polarizations form a checkerboard pattern. The first coil is placed relative to the magnet array such that legs of a coil segment of the first coil are positioned along respective boundaries between columns of the checkerboard pattern of alternating polarizations. The second coil is placed relative to the magnet array such that legs of a coil segment of the second coil are positioned along respective center lines of columns of the checkerboard pattern of alternating polarizations. A Lamb wave is generated when the first coil is excited with an electrical current and a shear horizontal wave (SH) is generated when the second coil is excited with an electrical current.

The legs of the coil segment of the first coil have a coil spacing between them and the legs of the coil segment of the second coil have the same coil spacing between them. The coil segment of the second coil is offset from the coil segment of the first coil by a half of the coil spacing.

The EMAT may further include a printed circuit board (PCB). The first coil is on a first layer of the PCB and the second coil is on a second layer of the PCB. The magnet array is overlaid over the PCB.

The first coil may include a plurality of coil segments, each leg of the coil segments of the first coil being positioned along respective boundaries between columns of the checkerboard pattern of alternating polarizations. The second coil may include a plurality of coil segments, each leg of the coil segments of the second coil being positioned along respective center lines of columns of the checkerboard pattern of alternating polarizations.

The magnets of the magnet array may be block shaped, stepped magnets conforming to a curvature of a non-planar surface. The magnets of the magnet array may form an arc segment conforming to a curvature of a non-planar surface.

The magnets of the magnet array may have a rectangular or square footprint.

Another EMAT includes a magnet array and a coil. The magnet array has magnets with alternating polarizations. The magnets are arranged in columns and rows so that the alternating polarizations form a checkerboard pattern. At least one of the magnet array and the coil is movable between (i) a first position in which the coil is placed relative to the magnet array such that legs of a coil segment of the coil are positioned along respective boundaries between columns of the checkerboard pattern of alternating polarizations and (ii) a second position in which the coil is placed relative to the magnet array such that the legs of the coil segment of the coil are positioned along respective center lines of columns of the checkerboard pattern of alternating polarizations. A Lamb wave is generated when the coil is excited with an electrical current while in the first position and a SH wave is generated when the coil is excited with an electrical current while in the second position.

The legs of the coil segment of the coil have a coil spacing between them. The first position and the second position are offset from one another by a half of the coil spacing.

The coil may include a plurality of connected coil segments. Each leg of the coil segments of the coil being positioned along respective boundaries between columns of the checkerboard pattern of alternating polarizations when the coil is placed relative to the magnet array in the first position. Each leg of the coil segments of the coil being positioned along respective center lines of columns of the checkerboard pattern of alternating polarizations when the coil is placed relative to the magnet array in the second position.

The EMAT may further include an actuator configured to move at least one of (i) the magnet array relative to the coil and (ii) the coil relative to the magnet array.

Another EMAT includes a magnet array and a coil. The magnet array has magnets with alternating polarizations. The magnets are arranged in columns and rows so that the alternating polarizations form a checkerboard pattern. The coil is placed relative to the magnet array such that legs of a coil segment of the coil are positioned along respective boundaries between columns of the checkerboard pattern of alternating polarizations. A Lamb wave is generated when the coil is excited with an electrical current.

Another EMAT a magnet array, a coil, and a magnetic conducting material layer. The magnet array has magnets with alternating polarizations. The magnets are arranged in columns and rows so that the alternating polarizations form a checkerboard pattern. The magnetic conducting material layer is between the magnet array and the coil. The magnetic conducting material layer is configured to direct the checkerboard pattern of alternating polarizations of the magnet array to (i) a first position in which the coil is placed relative to the magnet array such that legs of a coil segment of the coil are positioned along respective boundaries between columns of the checkerboard pattern of alternating polarizations and (ii) a second position in which the coil is placed relative to the magnet array such that the legs of the coil segment of the coil are positioned along respective center lines of columns of the checkerboard pattern of alternating polarizations. A Lamb wave is generated when the coil is excited with an electrical current while in the first position and a shear horizontal wave is generated when the coil is excited with an electrical current while in the second position.

In this EMAT, at least one of the magnet array and the coil may be movable (i) for the coil to be placed relative to the magnet array such that legs of a coil segment of the coil are positioned along respective boundaries between columns of the checkerboard pattern of alternating polarizations and (ii) for the coil to be placed relative to the magnet array such that the legs of the coil segment of the coil are positioned along respective center lines of columns of the checkerboard pattern of alternating polarizations.

Embodiments of the present invention provide an EMAT in which the excitation of both Lamb waves and SH waves is merged into a design having one or more coils, a single magnet array, and a single PCB. The EMAT may be implemented in either a first design involving a multiplexing-coil arrangement or a second design involving either a moving magnet or moving coil arrangement. The selection of the first or second designs for implementing the EMAT depends on the application.

In the first design of the EMAT involving a multiplexing-coil arrangement, the EMAT includes a first electrical conductor coil, a second electrical conductor coil, a single permanent magnet array, and a single PCB. The first and second coils are fabricated onto first and second layers, respectively, of the PCB. The coils have identical spacing and are overlapped with each other with a shift of alignment by half the coil spacing. The coils have distinct electrode pads and can thus be excited independently. The magnet array is overlaid over the coils. The EMAT generates a Lamb wave when the first coil is excited with an electrical current. The EMAT generates a SH wave when the second coil is excited with an electrical current.

In the second design of the EMAT involving either a moving magnet or moving coil arrangement, the EMAT includes an electrical conductor coil, a single permanent magnet array, and a single PCB. The coil is fabricated onto a layer of the PCB. The magnet array is overlaid over the coil.

In the moving magnet arrangement of the second design, the magnet array is movable between a first position and a second position relative to the coil. The second position has a shift of alignment by half the coil spacing relative to the first position. The EMAT generates a Lamb wave when the coil is excited with an electrical current while the magnet array is in the first position relative to the coil. The EMAT generates a SH wave when the coil is excited with an electrical current while the magnet array is in the second position relative to the coil.

In the moving coil arrangement of the second design, the coil is movable between the first position and the second position relative to the magnet array. The EMAT generates a Lamb wave when the coil is excited with an electrical current while the coil is in the first position relative to the magnet array. The EMAT generates a SH wave when the coil is excited with an electrical current while the coil is in the second position relative to the magnet array.

BRIEF DESCRIPTION OF THE DRAWINGS

FIG. 7A illustrates a sketch of an EMAT having a moving magnet (or moving coil) arrangement for generating both Lamb waves and SH waves, the moving magnet (or moving coil) arrangement including an electrical conductor coil, a single permanent magnet array, and a single PCB, the sketch of FIG. 7A illustrating the coil on the PCB and the placement of the magnet array at a first position relative to the coil, the placement of the magnet array at the first position relative to the coil and the configuration of the magnet array being such that the EMAT generates a Lamb wave when the coil is excited with an electrical current;

FIG. 7B illustrates a sketch of the EMAT having the moving magnet (or moving coil) arrangement, the sketch of FIG. 7B illustrating the placement of the magnet array at a second position relative to the coil, the placement of the magnet array at the second position relative to the coil and the configuration of the magnet array being such that the EMAT generates a SH wave when the coil is excited with an electrical current;

FIG. 8A illustrates a sketch of a side view of an EMAT with the magnet array having block-shaped stepped magnets to conform to the curvature of a non-planar surface such as a pipe surface;

FIG. 8B illustrates a sketch of a side view of an EMAT with the magnet array having magnets in an arc segment to conform to the curvature of the non-planar surface.

DETAILED DESCRIPTION

Detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Referring now to FIGS. 1A, 1B, 2, 3, and 4, an electromagnetic acoustic transducer (EMAT) 10 having a multiplexing-coil arrangement for generating both Lamb waves and shear horizontal (SH) waves will be described. Per the multiplexing-coil arrangement, EMAT 10 includes a first electrical conductor coil 12, a second electrical conductor coil 14, a single permanent magnet array 16, and a single printed circuit board (PCB) 18.

Figure 1A:
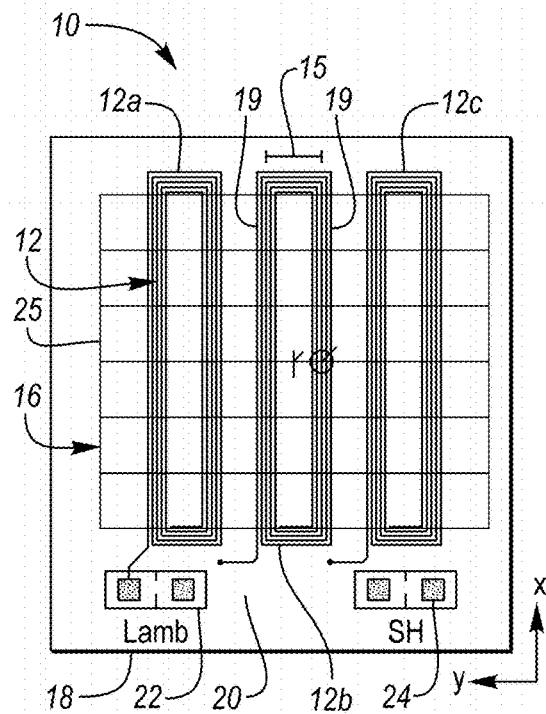
FIG. 1A illustrates a sketch of an electro-magnetic acoustic transducer (EMAT) having a multiplexing-coil arrangement for generating both Lamb waves and shear horizontal (SH) waves, the multiplexing-coil arrangement including a first electrical conductor coil, a second electrical conductor coil, a single permanent magnet array, and a single printed circuit board (PCB), the sketch of FIG. 1A illustrating the first coil on a first layer of the PCB and the placement of the first coil relative to the magnet array, the placement of the first coil relative to the magnet array and the configuration of the magnet array being such that the EMAT generates a Lamb wave when the first coil is excited with an electrical current.

FIG. 1A illustrates first coil 12 on a first layer 20 of PCB 18 and the placement of the first coil relative to magnet array 16. As described in detail below, the placement of first coil 12 relative to magnet array 16 as shown in FIG. 1A and the configuration of the magnet array is such that EMAT 10 generates a Lamb wave when the first coil is excited with an electrical current.

Figure 1B:
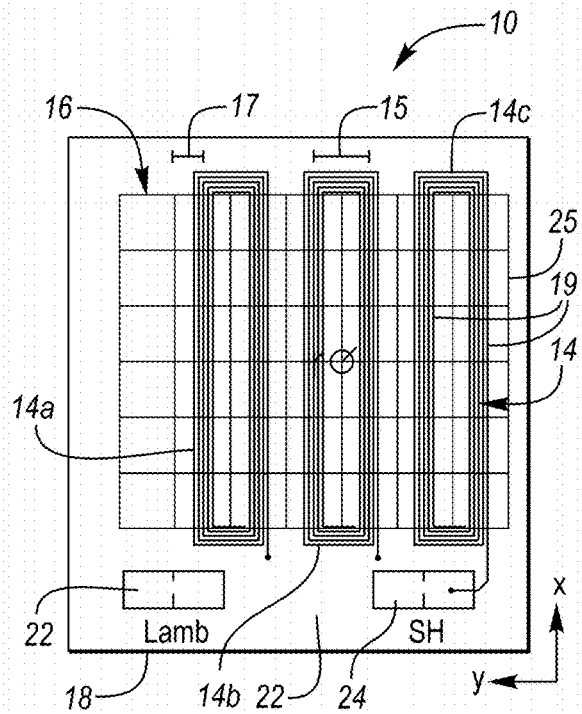
FIG. 1B illustrates a sketch of the EMAT having the multiplexing-coil arrangement, the sketch of FIG. 1B illustrating the second coil on a second layer of the PCB and the placement of the second coil relative to the magnet array, the placement of the second coil relative to the magnet array and the configuration of the magnet array being such that the EMAT generates a SH wave when the second coil is excited with an electrical current.

FIG. 1B illustrates second coil 14 on a second layer 22 of PCB 18 and the placement of the second coil relative to magnet array 16. As described in detail below, the placement of second coil 14 relative to magnet array 16 as shown in FIG. 1B and the configuration of the magnet array is such that EMAT 10 generates a SH wave when the second coil is excited with an electrical current.

First layer 20 and second layer 22 of PCB 18 are different layers of the PCB. PCB layers 20 and 22 overlap with each other, but are plotted separately in FIGS. 1A and 1B to provide a clear illustration of the layout of first coil 12 and second coil 14.

First coil 12 includes one or more serially connected coil segments and second coil 14 includes one or more serially connected coil segments. For example, as shown in FIG. 1A, first coil 12 includes three serially connected coil segments 12a, 12b, and 12c. As an example, second coil 14 has the identical coil configuration of first coil 12. As such, as shown in FIG. 1B, second coil 14 includes three serially connected coil segments 14a, 14b, and 14c. In other embodiments, first coil 12 and second coil 14 may have different amounts of coil segments from one another. Additionally, as an example, as shown in FIGS. 1A and 1B, each of first coil 12 and second coil 14 is a looped coil. In other embodiments, first coil 12 and/or second coil 14 is a meander coil.

Figure 2:
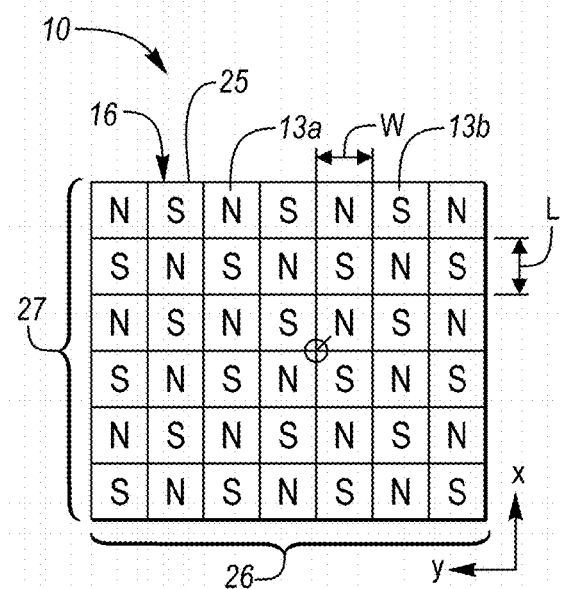
FIG. 2 illustrates a sketch of the magnet array.
Figure 3:
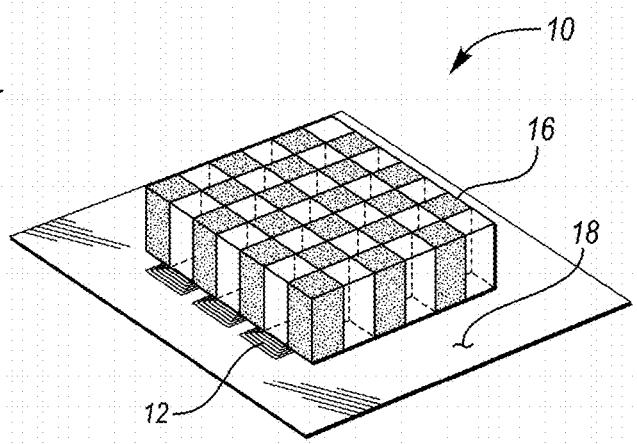
FIG. 3 illustrates a sketch of the EMAT with the magnet array arranged over the PCB.

FIG. 2 illustrates a sketch of magnet array 16. FIG. 3 illustrates a sketch of EMAT 10 with magnet array 16 assembled over PCB 18. Magnet array 16 includes a plurality of magnets which are arranged to form a grid 25. The magnets are further arranged within grid 25 so that their alternating magnetic polarizations (i.e., north (N) 13a and south (S) 13b) form a checkerboard pattern.

This checkerboard pattern of alternating magnetic polarizations can be generated above or towards the side of PCB 18. The whole arrangement of magnet array 16 can be offset from coils 12 and 14. If generated to the side the checkerboard pattern of alternating polarizations of magnet array 16 can be steered or redirected to PCB 18 by a magnetic conducting material layer 31 (shown in FIG. 8A). This magnetic conducting material 31 may be a soft magnetic composite that is ferromagnetic and non-conductive such as a ferromagnetic power coated with insulation materials and surrounded by organic binders like resin or rubber. The material has properties that redirect the magnetic field and is not limited to the above-mentioned material. In practice, this layer of such magnetic conducting layer 31 between magnet array 16 and PCB 18 can also serve the purpose of preventing mechanical wear of PCB surface insulation by the magnet array, especially when there is relative motion between both.

Grid 25 designates the arrangement of the magnets of magnet array 16. Grid 25 includes a plurality of columns 26 and a plurality of rows 27. As an example, grid 25 includes six columns 26 and seven rows 27. Each column/row pair (e.g., $(x_2, y_1)$, $(x_1, y_3)$, etc.) of grid 25 defines a respective space of the grid. A magnet of magnet array 16 with a polarization in the out-of-page direction is placed at each space of grid 25. The magnet has the same shape and size as the space of grid 25. Thus, magnet array 16 includes columns 26 of magnets and rows 27 of magnets. The magnets of magnet array 16 are placed at corresponding spaces of grid 25 such that their magnetic polarizations 13a and 13b change alternatively (N-S-N-S-etc.). Consequently, each magnet has the opposite polarization than its neighboring four magnets.

As an example, as indicated in FIGS. 1A, 1B, 2, and 3, the magnets of magnet array 16 have a square footprint which corresponds to the square perimeter of the spaces of grid 25. Each magnet of magnet array 16 has a length (L) and a width (W) (designated in FIG. 2). The length (L) and the width (W) for each magnet are the same because the magnets have a square footprint. An advantage of having square magnets in magnet array 16 is that the square magnet configuration optimizes acoustic wave strength.

Herein, as a convention, the length (L) runs along the x-direction and the width (W) runs along the y-direction. Further, as described in greater detail herein, the x-direction is the wave propagation direction and the y-direction is the in-plane transverse direction.

In other embodiments, the magnets of magnet array 16 have a circular or rectangular footprint. In the embodiments in which the magnets have a non-square, rectangular perimeter, the spaces of grid 25 correspondingly have the non-square, rectangular perimeter. Thus, in these embodiments, the length (L) differs from the width (W) for each magnet. For instance, as indicated by an exemplary mesh of grid 25 shown in FIG. 4, the spaces of the grid have a non-square, rectangular perimeter with the width (W) being larger than the length (L). In other embodiments, the width (W) of the magnets is different across two or more columns of magnets of magnet array 16. In other embodiments, the magnets of magnet array 16 include two or more of circular, rectangular, and square footprints. This could mean, for instance, that some of the magnets have rectangular footprints and other ones of the magnets have square footprints.

In sum, magnet array 16 includes a plurality of magnets arranged in columns 26 and rows 27 with each magnet being placed at a corresponding column/row pair. As such, magnet array 16 includes columns 26 of magnets and rows 27 of magnets. Columns 26 of magnets are separated from neighboring columns 26 of magnets along vertical interfaces or boundaries 28 of grid 25 (designated in FIG. 4). Similarly, rows 27 of magnets are separated from neighboring rows 27 of magnets along horizontal interfaces or boundaries 29 of grid 25 (designated in FIG. 4).

As shown in FIGS. 1A and 1B, coil segments 12a, 12b, and 12c of first coil 12 and coil segments 14a, 14b, and 14c of second coil 14 have a length running in the x-direction and a width running in the y-direction. In this embodiment, the length of the coil segments is longer than the width of the coil segments.

Each coil segment has a pair of opposed long, straight legs 19 running along the length of the coil segment. Legs 19 are separated in the y-direction from one another by a coil spacing 15. Coil spacing 15 is the same spacing (i.e., the same width) for all coil segments of first coil 12 and second coil 14. Thus, each coil segment of first coil 12 and each coil segment of second coil 14 has a pair of opposed long, straight legs 19 running in the x-direction which are separated from one another by the same coil spacing 15 running in the y-direction.

Figure 4:
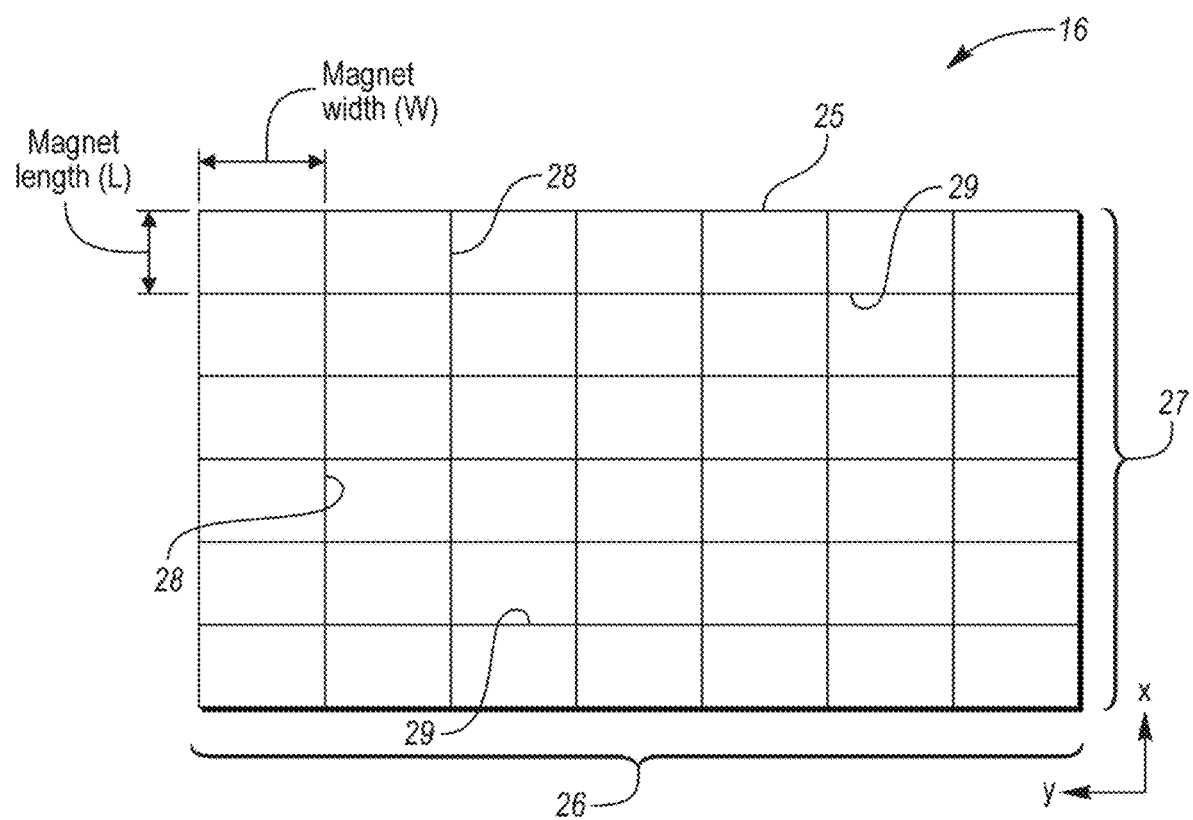
FIG. 4 illustrates a sketch of an exemplary mesh grid of the magnet array.

As shown in FIG. 1A, and referring to FIGS. 2 and 4, the placement of first coil 12 relative to magnet array 16 is such that each leg 19 of each coil segment of the first coil is positioned along a respective boundary line between two columns of magnets of the magnet array. Each magnet of the column of magnets on one side of a boundary line has an opposite polarity to the magnet in the same row in the column of magnets on the other side of the boundary line.

Put another way, each leg 19 of each coil segment of first coil 12 is positioned along a respective vertical interface 28 between two columns of magnets of the magnet array. More particularly, legs 19 of coil segment 12a are positioned along a first set of respective neighboring vertical interfaces 28; legs 19 of coil segment 12b are positioned along a second set of respective neighboring vertical interfaces 28; and legs 19 of coil segment 12c are positioned along a third set of respective neighboring vertical interfaces 28.

Consequently, as each leg 19 of a coil segment of first coil 12 is positioned along a respective boundary line between two columns of magnets of the magnet array, as the legs of the coil segment are separated by coil spacing 15, and as the width of each column of magnets is the width (W) of the magnets, the width of coil spacing 15 is the same width as the width (W) for each magnet of magnet array 16 (i.e., coil spacing=magnet width).

As shown in FIG. 1B, and referring to FIGS. 2 and 4, the placement of second coil 14 relative to magnet array 16 is such that each leg 19 of each coil segment of the second coil is positioned along a center line of a respective column of magnets of the magnet array.

Put another way, each leg 19 of each coil segment of second coil 14 is positioned between a respective set of neighboring vertical interfaces 28 bounding a column of magnets of the magnet array. More particularly, legs 19 of coil segment 14a are positioned between a first set of neighboring vertical interfaces 28 bounding a column of magnets of the magnet array; legs 19 of coil segment 14b are positioned between a second set of neighboring vertical interfaces 28 bounding another column of magnets of the magnet array; and legs 19 of coil segment 14c are positioned between a third set of neighboring vertical interfaces 28 bounding another column of magnets of the magnet array.

Consequently, as legs 19 of the coil segments of second coil 14 are positioned along respective center lines of columns of magnets of the magnet array, as legs 19 of the coil segments of first coil 12 are positioned along respective boundary lines of columns of magnets of the magnet array, and as the legs of all the coil segments are separated by coil spacing 15, first coil 12 and second coil 14 are shifted in alignment with each other by a half 17 of coil spacing 15 (i.e., coil shift (offset)=½ *coil spacing=½*magnet width).

As seen from a comparison of FIGS. 1A and 1B, first coil 12 and second coil 14 are overlapped with each other with a shift of alignment by half 17 of coil spacing 15. Magnet array 16 is overlaid over coils 12 and 14 as the magnet array is assembled over PCB 18.

As further shown in FIGS. 1A and 1B, PCB 18 includes a first electrode pad 22 for first coil 12 and a second electrode pad 24 for second coil 14. The two ends of first coil 12 are connected to first electrode pad 22. First coil 12 can be excited with an electrical current applied to first electrode pad 22. The two ends of second coil 14 are connected to second electrode pad 24. Second coil 14 can be excited with an electrical current applied to second electrode pad 24. As such, coils 12 and 14 have distinct electrode pads 22 and 24, respectively, and can thus be excited independently.

First coil 12 on first layer 20 of PCB 18 is for Lamb wave generation. EMAT 10 generates a Lamb wave when first coil 12 is excited with an electrical current. Second coil 14 on second layer 22 of PCB 18 is for SH wave generation. EMAT 10 generates a SH wave when second coil 14 is excited with an electrical current.

As seen from a comparison between FIGS. 1A and 1B, first coil 12 and second coil 14 have the same dimension and are aligned in the same direction, but have a shift in alignment with magnet array 16. This is the reason why two types of waves are excited. That is, this is the reason why first coil 12 generates a Lamb wave when the first coil is excited and why second coil 14 generates a SH wave when the second coil is excited.

Figure 5A:
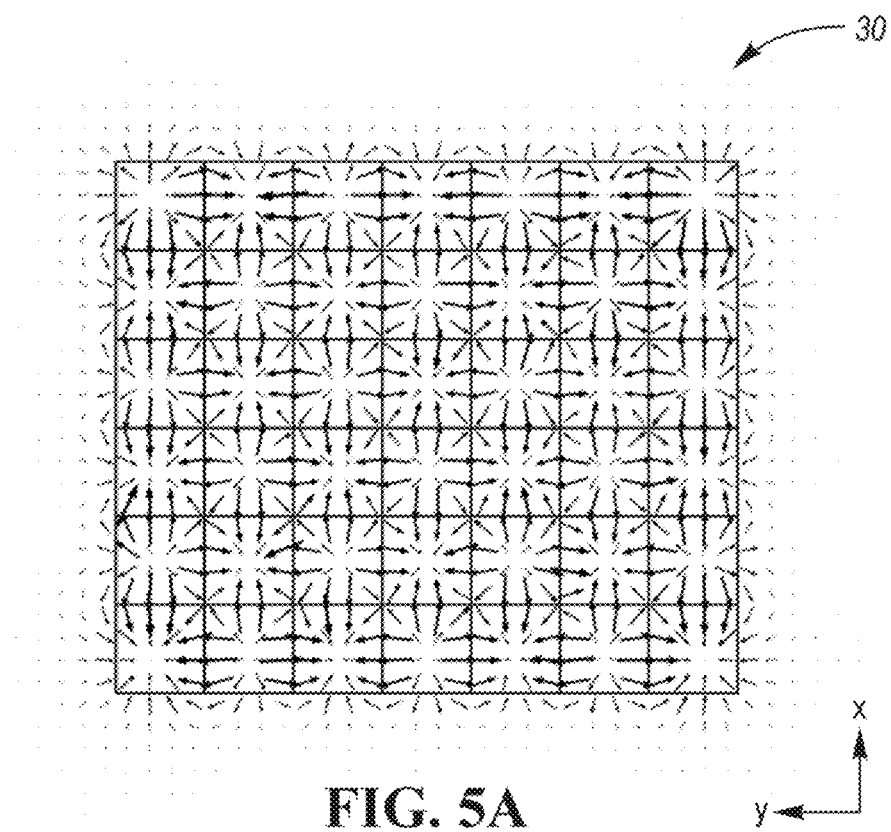
FIG. 5A illustrates a sketch of an in-plane magnetic flux density vector plot for the magnetic flux density distribution in a sample which is magnetized by the magnet array.
Figure 5B:
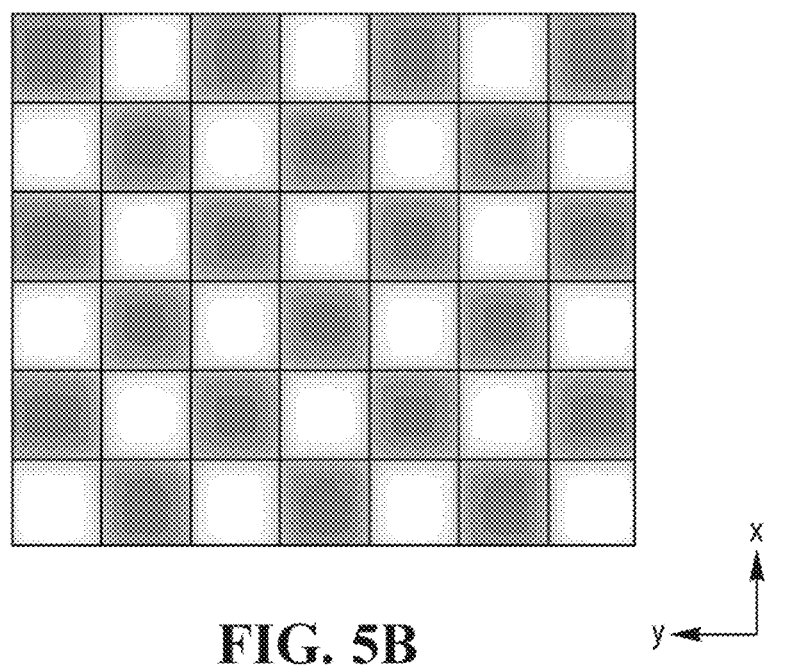
FIG. 5B illustrates a sketch of an out-of-plane magnetic flux density intensity plot for the magnetic flux density distribution in the sample which is magnetized by the magnet array.

Referring now to FIGS. 5A and 5B, a sketch 30 of an in-plane magnetic flux density vector plot for the magnetic flux density distribution in a sample which is magnetized by magnet array 16 is shown (FIG. 5A) and a sketch 40 of an out-of-plane magnetic flux density intensity plot for the magnetic flux density distribution in the sample which is magnetized by the magnet array is shown (FIG. 5B). In FIG. 5A, the magnetic flux density at a given location is proportional to the size of the arrow. Larger size arrows depict higher magnetic flux density whereas smaller size arrows depict lower magnetic flux density. In FIG. 5B, the dark shade means negative intensity whereas the light shade means positive intensity. The direction of the magnetic flux density is perpendicular to the plane of the page. The gray shade at the boundaries means zero intensity.

Per FIGS. 1A and 5A, it is observed that the electrical current through first coil 12 is subject to in-plane magnetic flux which results in out-of-plane Lorentz force which excites Lamb waves. On the other hand, per FIGS. 1B and 5B, the current through second coil 14 experiences the magnetic flux in out-of-plane direction which produces in-plane Lorentz force which excites SH waves.

Figure 6C:
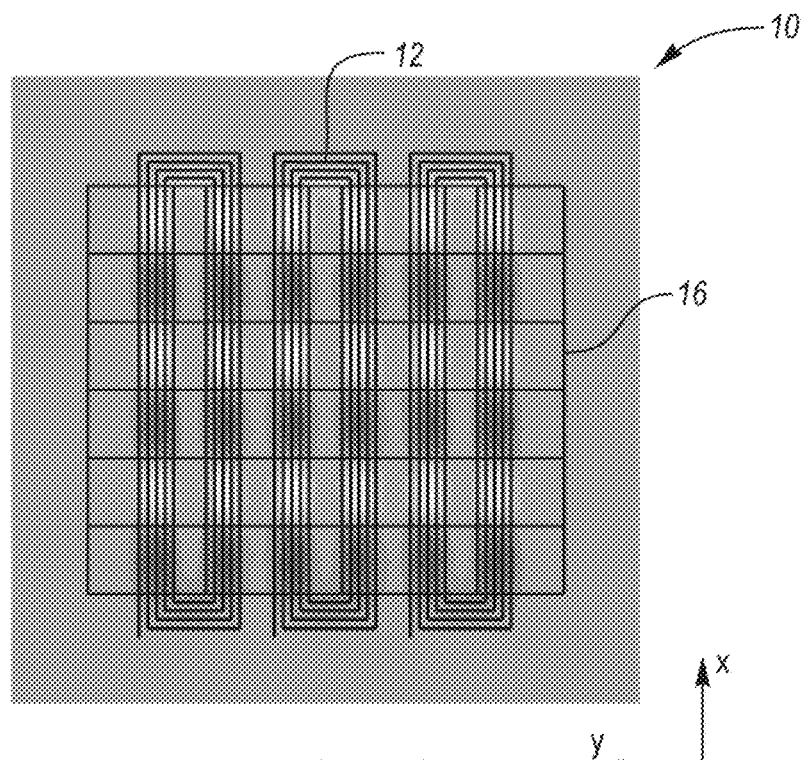
FIG. 6C illustrates a sketch of the distribution of resulting out-of-plane Lorentz force when the first coil is excited with an electrical current.
Figure 6A:
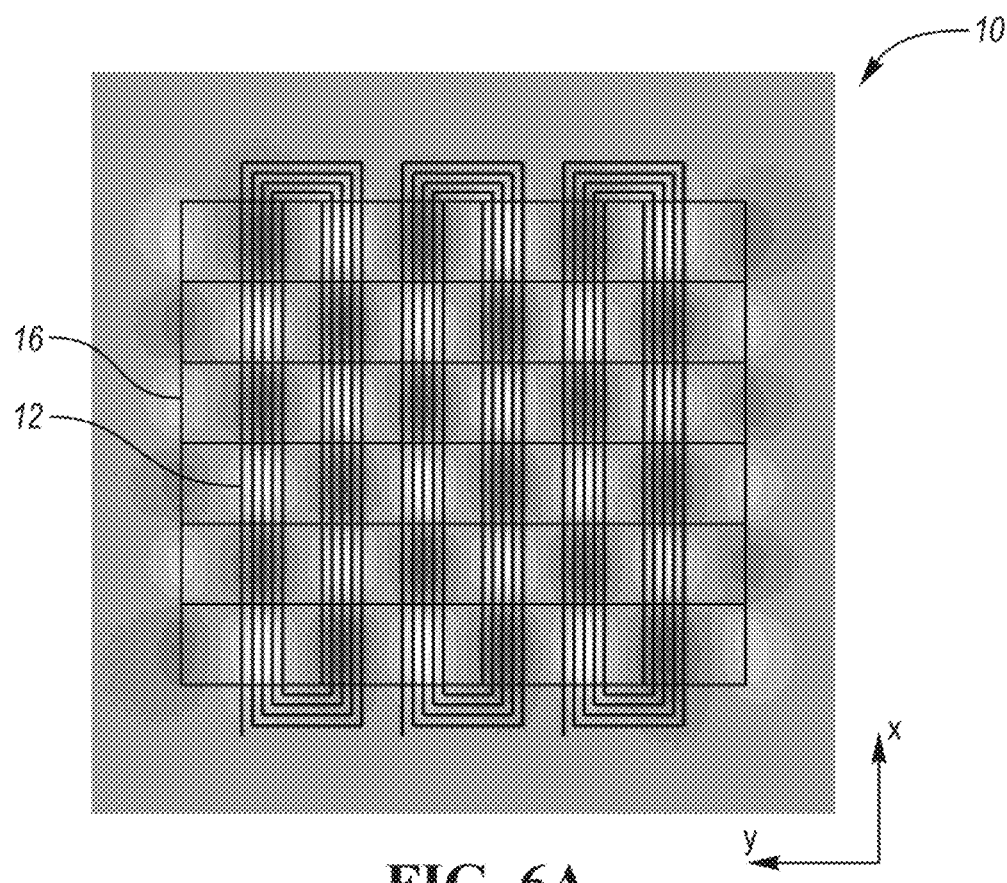
FIG. 6A illustrates a sketch of the distribution of in-plane magnetic flux density in the y-direction when the first coil is excited with an electrical current.
Figure 6B:
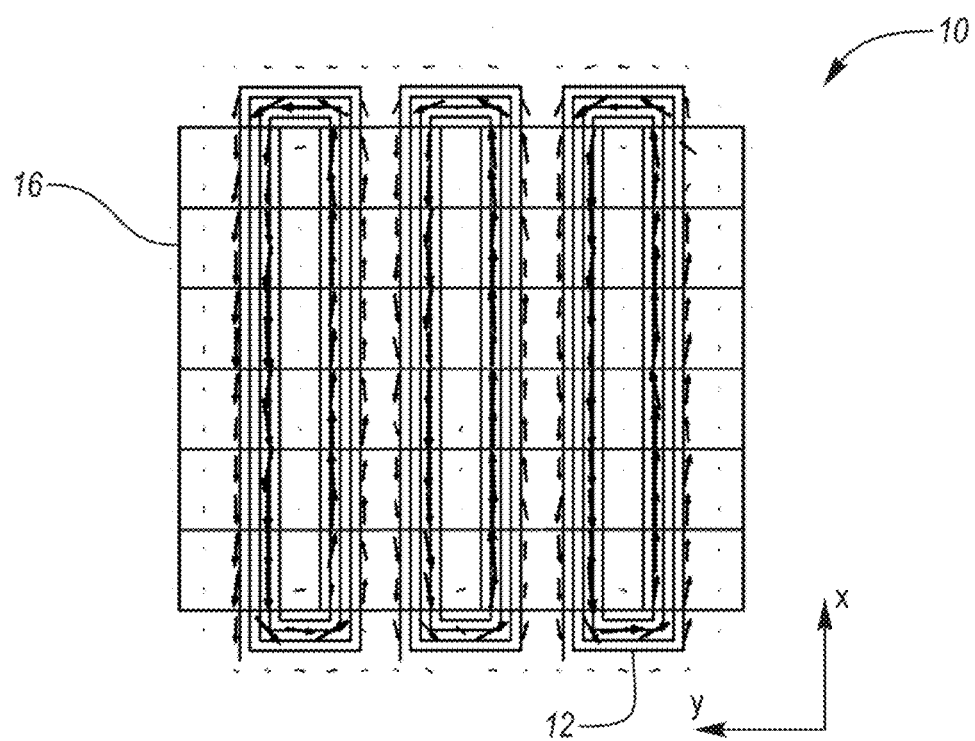
FIG. 6B illustrates a sketch of a vector plot of resulting in-plane current density in the material when the first coil is excited with an electrical current.

Referring now to FIGS. 6A, 6B, and 6C, with continual reference to FIG. 1A, the Lamb wave excitation using first coil 12 in conjunction with magnet array 16 will be described in further detail. FIG. 6A illustrates a sketch of the distribution of in-plane magnetic flux density in the y-direction when first coil 12 is excited with an electrical current. FIG. 6B illustrates a sketch of a vector plot of resulting in-plane current density in the material when first coil 12 is excited with an electrical current. FIG. 6C illustrates a sketch of the distribution of resulting out-of-plane Lorentz force when first coil 12 is excited with an electrical current.

The shades in FIG. 6A represent the magnetic flux density in the y-direction. The dark shade means negative intensity, the light shade means positive intensity, and the gray shade means zero intensity. The arrow sizes in FIG. 6B are proportional to density. The shades in FIG. 6C represent the magnitude of force with the dark shade meaning negative force and the light shade meaning positive force.

In FIG. 6A, the in-plane (in the plane of the material) magnetic flux has been superimposed on first coil 12 and geometries of magnets of magnet array 16 such that the different shades represent the flux intensity. The use of the in-plane magnetic flux results in out-of-plane Lorentz force. This is made possible by aligning the coil segments of first coil 12 along the boundaries between columns of magnets of magnet array 16.

The result of the placement of first coil 12 relative to the checkerboard-patterned magnet array 16 is the ability to produce a Lamb wave, wherein the Lorentz force acts normal to the conductive material instead of in-plane. The result of the normal Lorentz force is the ability to generate certain stronger wave modes such as the AO mode. This increases the signal to noise ratio of that wave mode. Another result from the arrangement is the generation of a Lamb wave whose wavelength is equal to twice the length (L) of the magnets (i.e., Lamb wave wavelength=2*magnet length).

Referring now to FIGS. 7A and 7B, an EMAT 50 having a moving magnet (or moving coil) arrangement for generating both Lamb waves and SH waves will be described. Per the moving magnet (or moving coil) arrangement, EMAT 50 includes first coil 12, magnet array 16, and PCB 18. Unlike EMAT 10 having the multiplexing-coil arrangement, EMAT 50 does not include second coil 14. Magnet array 16 is overlaid over first coil 12 as the magnet array is assembled over PCB 18. (Of course, alternatively, EMAT 50 includes second coil 14 and does not include first coil 12.)

FIG. 7A illustrates a sketch of first coil 12 on PCB 18 and the placement of magnet array 16 at a first position relative to the first coil. As shown in FIG. 7A, and referring to FIGS. 1A and 2, the placement of magnet array 16 at the first position relative to first coil 12 is such that each leg 19 of each coil segment of the first coil is positioned along a respective boundary line between two columns of magnets of the magnet array. This corresponds to the configuration of the multiplexing-coil arrangement shown in FIG. 1A for Lamb wave generation. Consequently, EMAT 50 generates a Lamb wave when first coil 12 is excited with an electrical current.

FIG. 7B illustrates a sketch of first coil 12 on PCB 18 and the placement of magnet array 16 at a second position relative to the first coil. As shown in FIG. 7B, and referring to FIGS. 1B, 2, and 7A, the placement of magnet array 16 at the second position relative to first coil 12 is at a shift of alignment by half 17 of coil spacing 15 compared to the placement of the magnet array at the first position relative to the first coil. This can be seen from a comparison between FIGS. 7A and 7B in which the first position and the second position have a shift of alignment by half 17 of coil spacing 15 relative to one another. Accordingly, the placement of magnet array 16 at the second position relative to first coil 12 is such that each leg 19 of each coil segment of the first coil is positioned along a center line of a respective column of magnets of the magnet array. This corresponds to the configuration of the multiplexing-coil arrangement shown in FIG. 1B for SH wave generation. Consequently, EMAT 50 generates a SH wave when first coil 12 is excited with an electrical current.

In the moving magnet arrangement, magnet array 16 is movable between the first position and the second position whereas PCB 18 with first coil 12 thereon remain fixed in position. For instance, the assembly for EMAT 50 includes an actuator 52 configured to mechanically move magnet array 16 between the first position and the second position.

In the moving coil arrangement, PCB 18 with first coil 12 thereon are movable between the first position and the second position whereas magnet array 16 remains fixed in position. For instance, actuator 52 is configured to mechanically move PCB 18 with first coil 12 thereon between the first position and the second position.

Referring now to FIG. 8A, a sketch of a side view of an EMAT 60 with magnet array 16 having block-shaped, stepped magnets is shown. The stepped configuration of the magnets conforms magnet array 16 to the curvature of a non-planar surface such as a surface of a pipe 62. First coil 12 of EMAT 60 is also shaped to conform to the curvature of the non-planar surface as shown in FIG. 8A. Although FIG. 8A illustrates the curvature in one-direction indicating an inner pipe wall, EMAT 60 can also be shaped to conform to the opposite curvature, i.e., an outer pipe wall. In the case of EMAT 60 involving the multiplexing-coil arrangement, second coil 14 of the EMAT is likewise shaped to conform to the curvature of the non-planar surface. Further, an understanding of magnet array 16 being overlaid first coil 12 (and second coil 14 when present) can be taken from the side view sketch of FIG. 8A.

Referring now to FIG. 8B, a sketch of a side view of EMAT 60 with magnet array 16 having magnets in an arc segment to conform to the curvature of the non-planar surface of pipe 62 is shown. The individual configuration of the magnets of magnet array 16 shown in FIG. 8B is different from the individual configuration of the magnets of magnet array 16 shown in FIG. 8A. In FIG. 8B each magnet has an arc to conform to the curvature of the non-planar surface.

EMAT 60 having its coil(s), magnet array 16, and PCB 18 conformed to a curved surface provides minimal clearance between the EMAT and the curved surface and hence maximizes the strength of the electromagnetic field that interacts with the non-planar material. Ultimately, this results in the production of a stronger guided wave and higher signal-to-noise ratio.

Figure 9:
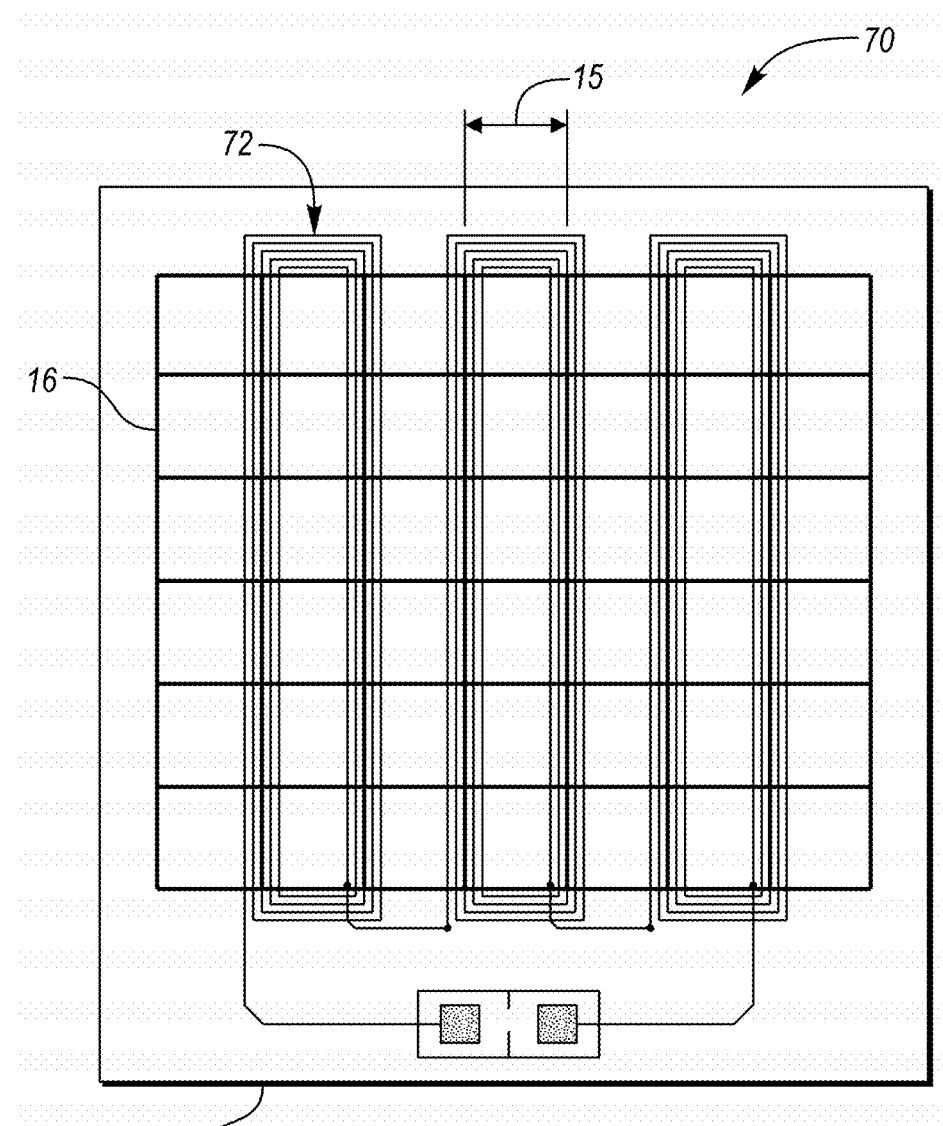
FIG. 9 illustrates a sketch of an EMAT having a single coil arrangement for generating Lamb waves only, the single coil arrangement including an electrical conductor coil, a single permanent magnet array, and a single PCB, the sketch of FIG. 9 illustrating the coil on the PCB and the placement of the coil relative to the magnet array, the placement of the coil relative to the magnet array and the configuration of the magnet array being such that the EMAT generates a Lamb wave when the coil is excited with an electrical current.

Referring now to FIG. 9, an EMAT 70 having a single coil arrangement for generating Lamb waves only is shown. Per the single coil arrangement. EMAT 70 includes a single electrical conductor coil 72, magnet array 16, and PCB 18. Magnet array 16 is overlaid coil 72 as the magnet array is assembled over PCB 18. As shown in FIG. 9, and referring to FIGS. 1A and 2, the placement of magnet array 16 relative to coil 72 is such that each leg of each coil segment of the coil is positioned along a respective boundary line between two columns of magnets of the magnet array. (This corresponds to the configuration of the multiplexing-coil arrangement shown in FIG. 1A for Lamb wave generation and to the configuration of the moving magnet (or moving coil) arrangement shown in FIG. 7A for Lamb wave generation.) Consequently, EMAT 70 generates a Lamb wave when coil 82 is excited with an electrical current.

As described, an EMAT in accordance with embodiments can generate a Lamb wave using a specific arrangement of a coil and a magnet array. The placement of the coil relative to the magnet array is such that each leg of the coil is positioned at a respective interface or boundary between two columns (or rows) of magnets of the magnet array with each magnet on one side of the interface or boundary being of opposite polarity to the magnet in the same row (or column) on the other side of the interface or boundary.

In moving magnet or moving coil embodiments, the magnet array is displaced with respect to the coil so that each leg of the coil is positioned along a respective center line of a column (or row) of magnets of the magnet array. In this position, the EMAT can generate a SH wave.

In multiplexing-coil embodiments, the EMAT further includes a second coil. The two coils are placed one over the other such that they are displaced from each other by a half a coil spacing. The two coils are electrically switched to activate one coil at a time. This produces the same effect as moving the magnet array or a coil with respect to one another to generate either Lamb wave or SH wave. As such, physical motion of any of the magnet array and the coil is eliminated. An advantage of the construction is that the EMAT is compact and the coils do not have to removed and rewound thus simplifying setup and operation. Further, more than two coils can be stacked.

EMATs in accordance with different embodiments may have different features. For instance, EMATs in accordance with exemplary embodiments described herein are focused on the excitation of Lamb and SH waves. However, depending on the structure where the guided waves are excited, the Rayleigh wave-Love wave combination can also be realized by the described moving magnet or moving coil arrangements and the described multiplexing-coil arrangement. Further, the exemplary embodiments described herein demonstrate two stacked coils, but more coils can be stacked to achieve goals like sending waves in different directions, improving wave strength, and exciting another wavelength so long as the magnet array arrangement is not changed. The design of the EMATs can be used on either flat or curved surfaces. A difference is that the coil(s) and magnet plan are adapted to the curvature of the surface. The shape of the magnets of the magnet array may be block shaped as illustrated herein, but can be any other shape, e.g., cylinder, if the magnet array provides the magnetic flux distribution having the patterns shown in FIGS. 5A and 5B.

Benefits of an EMAT in accordance with embodiments of the present invention include the following. Compared with typical EMATs, an EMAT in accordance with embodiments of the present invention can excite more types of guided waves and thus provide more potential and thus higher probability to detect defects. Compared with sensor heads having two EMATs to excite different types of guided waves, an EMAT in accordance with embodiments of the present invention has significantly reduced volume, footprint, and weight.

While exemplary embodiments are described above, it is not intended that these embodiments describe all possible forms of the present invention. Rather, the words used in the specification are words of description rather than limitation, and it is understood that various changes may be made without departing from the spirit and scope of the present invention. Additionally, the features of various implementing embodiments may be combined to form further embodiments of the present invention.

What is claimed is:

1. An electro-magnetic acoustic transducer comprising:
   a magnet array having a plurality of magnets with alternating polarizations, the magnets being arranged in columns and rows so that the alternating polarizations form a checkerboard pattern;
   a first coil placed relative to the magnet array such that legs of a coil segment of the first coil extend parallel to a first direction across the rows of the checkerboard pattern of alternating polarizations and are positioned along respective boundaries between adjacent pairs of columns of the checkerboard pattern of alternating polarizations, wherein for each leg of the first coil positioned along a respective boundary between an adjacent pair of columns of the checkerboard pattern, a magnet of the magnet array is in one of the adjacent pair of columns of the checkerboard pattern on one side of the respective boundary in a given row of the checkerboard pattern and another magnet of the magnet array having an opposite polarization is in the other one of the adjacent pair of columns of the checkerboard pattern on the other side of the respective boundary in the given row of the checkerboard pattern;
   a second coil placed relative to the magnet array such that legs of a coil segment of the second coil extend parallel to the first direction across the rows of the checkerboard pattern of alternating polarizations and are positioned along respective center lines of columns of the checkerboard pattern of alternating polarizations, wherein for each leg of the second coil positioned along a respective center line of a column of the checkerboard pattern, a magnet of the magnet array is in the column of the checkerboard pattern with a portion of the magnet being on one side of the respective center line in a given row of the checkerboard pattern and a remaining portion of the same magnet being on the other side of the respective center line in the given row of the checkerboard pattern; and
   wherein a Lamb wave is generated when the first coil is excited with an electrical current and a shear horizontal wave is generated when the second coil is excited with an electrical current.

2. The electro-magnetic acoustic transducer of claim 1 wherein:
   the legs of the coil segment of the first coil have a coil spacing between them and the legs of the coil segment of the second coil have the coil spacing between them; and
   the coil segment of the second coil is offset from the coil segment of the first coil by a half of the coil spacing.

3. The electro-magnetic acoustic transducer of claim 1 further comprising:
   a printed circuit board; and
   wherein the first coil is on a first layer of the printed circuit board and the second coil is on a second layer of the printed circuit board.

4. The electro-magnetic acoustic transducer of claim 3 wherein:
   the magnet array is overlaid over the printed circuit board.

5. The electro-magnetic acoustic transducer of claim 1 wherein:
   the first coil includes a plurality of coil segments, each leg of the coil segments of the first coil extending parallel to the first direction across the rows of the checkerboard pattern of alternating polarizations and being positioned along respective boundaries between ad'acent pairs of columns of the checkerboard pattern of alternating polarizations.

6. The electro-magnetic acoustic transducer of claim 5 wherein:
   the second coil includes a plurality of coil segments, each leg of the coil segments of the second coil extending parallel to the first direction across the rows of the checkerboard pattern of alternating polarizations and being positioned along respective center lines of columns of the checkerboard pattern of alternating polarizations.

7. The electro-magnetic acoustic transducer of claim 1 wherein:
the magnets of the magnet array are block shaped, stepped magnets conforming to a curvature of a non-planar surface.

8. The electro-magnetic acoustic transducer of claim 1 wherein:
the magnets of the magnet array form an arc segment conforming to a curvature of a non-planar surface.

9. The electro-magnetic acoustic transducer of claim 1 wherein:
the magnets of the magnet array have a rectangular footprint.

10. The electro-magnetic acoustic transducer of claim 1 wherein:
the magnets of the magnet array have a square footprint.

11. An electro-magnetic acoustic transducer comprising:
a magnet array having a plurality of magnets with alternating polarizations, the magnets being arranged in columns and rows so that the alternating polarizations form a checkerboard pattern;
a coil;
wherein at least one of the magnet array and the coil is movable between (i) a first position in which the coil is placed relative to the magnet array such that legs of a coil segment of the coil extend parallel to a first direction across the rows of the checkerboard pattern of alternating polarizations and are positioned along respective boundaries between adjacent pairs of columns of the checkerboard pattern of alternating polarizations, wherein for each leg of the coil positioned along a respective boundary between an adjacent pair of columns of the checkerboard pattern, a magnet of the magnet array is in one of the adjacent pairs of columns of the checkerboard pattern on one side of the respective boundary in a given row of the checkerboard pattern and another magnet of the magnet array having an opposite polarization is in the other one of the adjacent pair of columns of the checkerboard pattern on the other side of the respective boundary in the given row of the checkerboard pattern, and (ii) a second position in which the coil is placed relative to the magnet array such that the legs of the coil segment of the coil extend parallel to the first direction across the rows of the checkerboard pattern of alternating polarizations and are positioned along respective center lines of columns of the checkerboard pattern of alternating polarizations, wherein for each leg of the coil positioned along a respective center line of a column of the checkerboard pattern, a magnet of the magnet array is in the column with a portion of the magnet being on one side of the respective center line in a given row of the checkerboard pattern and a remaining portion of the same magnet being on the other side of the respective center line in the given row of the checkerboard pattern; and
wherein a Lamb wave is generated when the coil is excited with an electrical current while in the first position and a shear horizontal wave is generated when the coil is excited with an electrical current while in the second position.

12. The electro-magnetic acoustic transducer of claim 11 wherein:
the legs of the coil segment of the coil have a coil spacing between them; and
the first position and the second position are offset from one another by a half of the coil spacing.

13. The electro-magnetic acoustic transducer of claim 11 further comprising:
a printed circuit board;
wherein the coil is on a layer of the printed circuit board; and
wherein the magnet array is overlaid over the printed circuit board.

14. The electro-magnetic acoustic transducer of claim 11 wherein:
the coil includes a plurality of coil segments, each leg of the coil segments of the coil extending parallel to the first direction across the rows of the checkerboard pattern of alternating polarizations and being positioned along respective boundaries between adjacent pairs of columns of the checkerboard pattern of alternating polarizations when the coil is placed relative to the magnet array in the first position, and each leg of the coil segments of the coil extending parallel to the first direction across the rows of the checkerboard pattern of alternating polarizations and being positioned along respective center lines of columns of the checkerboard pattern of alternating polarizations when the coil is placed relative to the magnet array in the second position.

15. The electro-magnetic acoustic transducer of claim 11 wherein:
the magnets of the magnet array have a rectangular footprint.

16. The electro-magnetic acoustic transducer of claim 11 further comprising:
an actuator configured to move at least one of (i) the magnet array relative to the coil and (ii) the coil relative to the magnet array.

17. An electro-magnetic acoustic transducer comprising:
a magnet array having a plurality of magnets with alternating polarizations, the magnets being arranged in columns and rows so that the alternating polarizations form a checkerboard pattern;
a coil placed relative to the magnet array such that legs of a coil segment of the coil extend parallel to a first direction across the rows of the checkerboard pattern of alternating polarizations and are positioned along respective boundaries between adjacent pairs of columns of the checkerboard pattern of alternating polarizations, wherein for each leg of the coil positioned along a respective boundary between an adjacent pair of columns of the checkerboard pattern, a magnet of the magnet array is in one of the adjacent pairs of columns of the checkerboard pattern on one side of the respective boundary in a given row of the checkerboard pattern and another magnet of the magnet array having an opposite polarization is in the other one of the adjacent pair of columns of the checkerboard pattern on the other side of the respective boundary in the given row of the checkerboard pattern; and
wherein a Lamb wave is generated when the coil is excited with an electrical current.

18. The electro-magnetic acoustic transducer of claim 17 wherein:
the magnets of the magnet array have a rectangular footprint.

19. An electro-magnetic acoustic transducer comprising:
a magnet array having a plurality of magnets with alternating polarizations, the magnets being arranged in columns and rows so that the alternating polarizations form a checkerboard pattern;
a coil;
a magnetic conducting material layer between the magnet array and the coil, the magnetic conducting material layer configured to direct the checkerboard pattern of alternating polarizations of the magnet array to (i) a first position in which the coil is placed relative to the magnet array such that legs of a coil segment of the coil extend parallel to a first direction across the rows of the checkerboard pattern of alternating polarizations and are positioned along respective boundaries between adjacent pairs of columns of the checkerboard pattern of alternating polarizations, wherein for each leg of the coil positioned along a respective boundary between an adjacent pair of columns of the checkerboard pattern, a magnet of the magnet array is in one of the adjacent pair of columns of the checkerboard pattern on one side of the respective boundary in a given row of the checkerboard pattern and another magnet of the magnet array having an opposite polarization is in the other one of the adjacent pair of columns of the checkerboard pattern on the other side of the respective boundary in the given row of the checkerboard pattern, and (ii) a second position in which the coil is placed relative to the magnet array such that the legs of the coil segment of the coil extend parallel to the first direction across the rows of the checkerboard pattern of alternating polarizations and are positioned along respective center lines of columns of the checkerboard pattern of alternating polarizations, wherein for each leg of the coil positioned along a respective center line of a column of the checkerboard pattern, a magnet of the magnet array is in the column of the checkerboard pattern with a portion of the magnet being on one side of the respective center line in a given row of the checkerboard pattern and a remaining portion of the same magnet being on the other side of the respective center line in the given row of the checkerboard pattern; and
wherein a Lamb wave is generated when the coil is excited with an electrical current while in the first position and a shear horizontal wave is generated when the coil is excited with an electrical current while in the second position.

20. The electro-magnetic acoustic transducer of claim 19 wherein:
at least one of the magnet array and the coil is movable (i) for the coil to be placed relative to the magnet array such that legs of a coil segment of the coil extend parallel to a first direction across the rows of the checkerboard pattern of alternating polarizations and are positioned along respective boundaries between adjacent pairs of columns of the checkerboard pattern of alternating polarizations and (ii) for the coil to be placed relative to the magnet array such that the legs of the coil segment of the coil extend parallel to the first direction across the rows of the checkerboard pattern of alternating polarizations and are positioned along respective center lines of columns of the checkerboard pattern of alternating polarizations.

* * * * *

UNITED STATES PATENT AND TRADEMARK OFFICE
CERTIFICATE OF CORRECTION

PATENT NO. : 10,502,714 B2
APPLICATION NO. : 15/719022
DATED : December 10, 2019
INVENTOR(S) : Baiyang Ren et al.

Page 1 of 1

It is certified that error appears in the above-identified patent and that said Letters Patent is hereby corrected as shown below:

In the Claims

Column 12, Lines 60 – 61, Claim 5:
After "along respective boundaries between"
Delete "ad'acent" and
Insert -- adjacent --.

Signed and Sealed this
Twenty-fourth Day of March, 2020

Andrei Iancu
*Director of the United States Patent and Trademark Office*